(12) United States Patent
Xu et al.

(10) Patent No.: US 12,065,401 B1
(45) Date of Patent: Aug. 20, 2024

(54) INTEGRATED PROCESSES AND SYSTEMS FOR PRODUCING PARA-XYLENES

(71) Applicant: Saudi Arabian Oil Company, Dhahran (SA)

(72) Inventors: Qi Xu, Dhahran (SA); Veera Venkata Ramakrishna Tammana, Dhahran (SA); Mohammed I. Alamer, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 7 days.

(21) Appl. No.: 18/183,294

(22) Filed: Mar. 14, 2023

(51) Int. Cl.
*C07C 5/27* (2006.01)
*B01J 29/18* (2006.01)
(Continued)

(52) U.S. Cl.
CPC .............. *C07C 5/2737* (2013.01); *B01J 29/18* (2013.01); *B01J 29/40* (2013.01); *C07C 2/66* (2013.01);
(Continued)

(58) Field of Classification Search
CPC .......... C07C 5/2737; C07C 2/66; C07C 4/18; C07C 6/126; C07C 7/005; C07C 7/11;
(Continued)

(56) References Cited

U.S. PATENT DOCUMENTS

| | | |
|---|---|---|
| 4,310,715 A | 1/1982 | Dorawala et al. |
| 5,847,256 A | 12/1998 | Ichioka et al. |

(Continued)

FOREIGN PATENT DOCUMENTS

WO  2020086740 A1  4/2020

OTHER PUBLICATIONS

Notification of Transmittal of the International Search Report and the Written Opinion of the International Searching Authority, or the Declaration dated Mar. 20, 2024 pertaining to International application No. PCT/US2023/081826 filed Nov. 30, 2023, pp. 1-12.

*Primary Examiner* — In Suk C Bullock
*Assistant Examiner* — Jason Y Chong
(74) *Attorney, Agent, or Firm* — DINSMORE & SHOHL LLP

(57) ABSTRACT

An integrated process for producing para-xylenes may include catalytically reforming a naphtha feed stream; separating the reformate stream into a $C_1$-$C_7$ hydrocarbon stream and a $C_{8+}$ hydrocarbon stream; exposing the $C_1$-$C_7$ hydrocarbon stream to a first solvent in a solvent extraction unit to form a non-aromatic hydrocarbon stream and an aromatics stream; upgrading the aromatics stream to form a toluene-rich transalkylation feed stream; separating the $C_{8+}$ hydrocarbon stream into a $C_{9+}$ hydrocarbon stream, a para-xylene stream and a xylene isomer stream; dealkylating the $C_{9+}$ hydrocarbon stream; separating the dealkylation product stream into an additional xylene stream and a tri-methyl benzene rich stream; and upgrading the toluene-rich transalkylation feed stream and the tri-methyl benzene rich stream with a hydrogen stream to produce an alkyl-benzene stream and additional xylene stream, wherein a ratio by weight of the toluene-rich transalkylation feed stream to the tri-methylbenzene rich stream is from 0.3 to 3.

13 Claims, 3 Drawing Sheets

(51) Int. Cl.
  *B01J 29/40*   (2006.01)
  *C07C 2/66*    (2006.01)
  *C07C 4/18*    (2006.01)
  *C07C 6/12*    (2006.01)
  *C07C 7/00*    (2006.01)
  *C07C 7/11*    (2006.01)

(52) U.S. Cl.
  CPC .............. *C07C 4/18* (2013.01); *C07C 6/126* (2013.01); *C07C 7/005* (2013.01); *C07C 7/11* (2013.01); *C07C 2523/28* (2013.01); *C07C 2523/30* (2013.01); *C07C 2523/42* (2013.01); *C07C 2523/44* (2013.01); *C07C 2523/72* (2013.01); *C07C 2523/75* (2013.01); *C07C 2523/755* (2013.01); *C07C 2529/18* (2013.01); *C07C 2529/40* (2013.01)

(58) Field of Classification Search
  CPC ............ C07C 2523/28; C07C 2523/30; C07C 2523/42; C07C 2523/44; C07C 2523/72; C07C 2523/75; C07C 2523/755; C07C 2529/18; C07C 2529/40; B01J 29/18; B01J 29/40
  See application file for complete search history.

(56) References Cited

U.S. PATENT DOCUMENTS

| | | | |
|---|---|---|---|
| 11,279,663 | B2 | 3/2022 | Koseoglu et al. |
| 2013/0144097 | A1 | 6/2013 | Bender et al. |
| 2013/0165719 | A1 | 6/2013 | Negiz et al. |
| 2018/0186710 | A1 | 7/2018 | Abudawoud et al. |
| 2018/0265429 | A1 | 9/2018 | Krimsky et al. |
| 2019/0106367 | A1* | 4/2019 | Carter ............... C07C 6/06 |
| 2021/0017102 | A1* | 1/2021 | Nair ............... B01J 23/36 |
| 2021/0032182 | A1* | 2/2021 | Molinier ............... C10G 50/00 |
| 2021/0122689 | A1 | 4/2021 | Xu et al. |
| 2022/0274900 | A1 | 9/2022 | Tinger et al. |

\* cited by examiner

INTEGRATED PROCESSES AND SYSTEMS FOR PRODUCING PARA-XYLENES

TECHNICAL FIELD

Embodiments of the present disclosure generally relate to refining and upgrading hydrocarbon oil, and pertain particularly to an integrated process and system for upgrading a naphtha stream into para-xylenes.

BACKGROUND

Aromatic compounds, such as benzene, toluene, and xylenes (BTX), are basic intermediates for many petrochemical industries. Particularly desired are p-xylenes, a xylene isomer of the group 1,2-dimethylbenzene, (ortho-xylene or o-xylene), 1,3-dimethylbenzene (meta-xylene or m-xylene), or 1,4-dimethylbenzene (para-xylene or p-xylene). Para-xylenes may be used as a raw material in the synthesis of commercial plastics in clothing fibers, liquid and food storage containers, and thermoforming for manufacturing, among other uses. Accordingly, methods of converting entire hydrocarbon feeds into para-xylenes are desired.

SUMMARY

In typical BTX-generating refinery processes, a naphtha feed is first sent to a catalytic reformer. The catalytic reformer reforms the naphtha stream into a reformate stream that is aromatics-rich. The reformate stream is then typically separated into light (carbon content less than 8) and heavy (carbon content greater than 7) streams.

However, aromatic compounds with carbon contents greater than 9 ($C_{10+}$) may ordinarily be purged from the heavy stream and not utilized in any manner, due to these streams being thought of as petroleum coke precursors, potentially deactivating catalysts, as well as building up as unconverted fractions in recycling streams. As hydrocarbon streams, and the subset of naphtha streams, may contain a large percentage of these $C_{10+}$ fractions, considerable amounts of p-xylene and other xylene isomers are not capitalized on within existing processes. Accordingly, methods are desired for converting $C_{10+}$ fractions in naphtha streams, so as to utilize the entire naphtha stream and maximize para-xylene yields.

Consequently, described herein are integrated processes and systems for producing para-xylenes from a naphtha feed stream, while providing the aforementioned benefits. Particularly, $C_{10+}$ fractions may be converted using a combination of de-alkylation and hydro-dearylation reactions, resulting in increased xylene and toluene yield, the increased toluene yield of which may be converted to benzene and further increased xylene yield in downstream transalkylation and disproportionation. In this way, the entire heavy fraction of the naphtha feed stream may be converted to xylene isomers, and in particular, para-xylene.

In accordance with one embodiment herein, an integrated process for producing para-xylenes may include catalytically reforming a naphtha feed stream to form a reformate stream; separating the reformate stream into a $C_1$-$C_7$ hydrocarbon stream and a $C_{8+}$ hydrocarbon stream; exposing the $C_1$-$C_7$ hydrocarbon stream to a first solvent in a solvent extraction unit to form a non-aromatic hydrocarbon stream and an aromatics stream; upgrading the aromatics stream to form a toluene-rich transalkylation feed stream; separating the $C_{8+}$ hydrocarbon stream into a $C_{9+}$ hydrocarbon stream and a xylene stream; separating the xylene stream into a para-xylene stream and a xylene isomer stream; isomerizing the xylene isomer stream with a isomerization catalyst to produce a para-xylene rich stream; dealkylating the $C_{9+}$ hydrocarbon stream in an dealkylation unit with a dealkylation catalyst, thereby forming a dealkylated product stream; separating the dealkylation product stream into an additional aromatics stream, an additional xylene stream, and a tri-methyl benzene rich stream; and upgrading the toluene-rich transalkylation feed stream and the tri-methyl benzene rich stream in a transalkylation unit with a hydrogen stream and a transalkylation catalyst to produce an alkyl-benzene stream and additional amounts of non-aromatic hydrocarbon stream, aromatics stream, and xylene stream, and wherein a ratio by weight of the toluene-rich transalkylation feed stream to the tri-methylbenzene rich stream is from 0.3 to 3.

In accordance with another embodiment herein, an integrated system for producing para-xylenes includes a catalytic reformer including a reforming catalyst; a first separator fluidly connected to the catalytic reformer and downstream from the catalytic reformer; a solvent extraction unit including a first solvent, the solvent extraction unit fluidly connected to and downstream from the first separator; a toluene generation unit fluidly connected to and downstream from the solvent extraction unit; a xylene separation unit fluidly connected to and downstream from the first separator; a dealkylation unit including a dealkylation catalyst, the dealkylation unit fluidly connected to and downstream from the xylene separation unit; a fourth separator fluidly connected to and downstream from the dealkylation unit; a transalkylation unit including a transalkylation catalyst, the transalkylation unit fluidly connected to and downstream from the toluene generation unit and the fourth separator; a p-xylene separation unit fluidly connected to and downstream from the xylene separation unit and the fourth separator; and a xylene isomerization unit including a isomerization catalyst, the xylene isomerization unit fluidly connected to, downstream from, and upstream from the p-xylene separation unit.

Additional features and advantages of the embodiments described herein will be set forth in the detailed description which follows, and in part will be readily apparent to those skilled in the art from that description or recognized by practicing the embodiments described, including the detailed description and the claims which are provided infra.

BRIEF DESCRIPTION OF THE DRAWINGS

The following detailed description of specific embodiments of the present disclosure can be best understood when read in conjunction with the following drawings in which.

Figure 1:
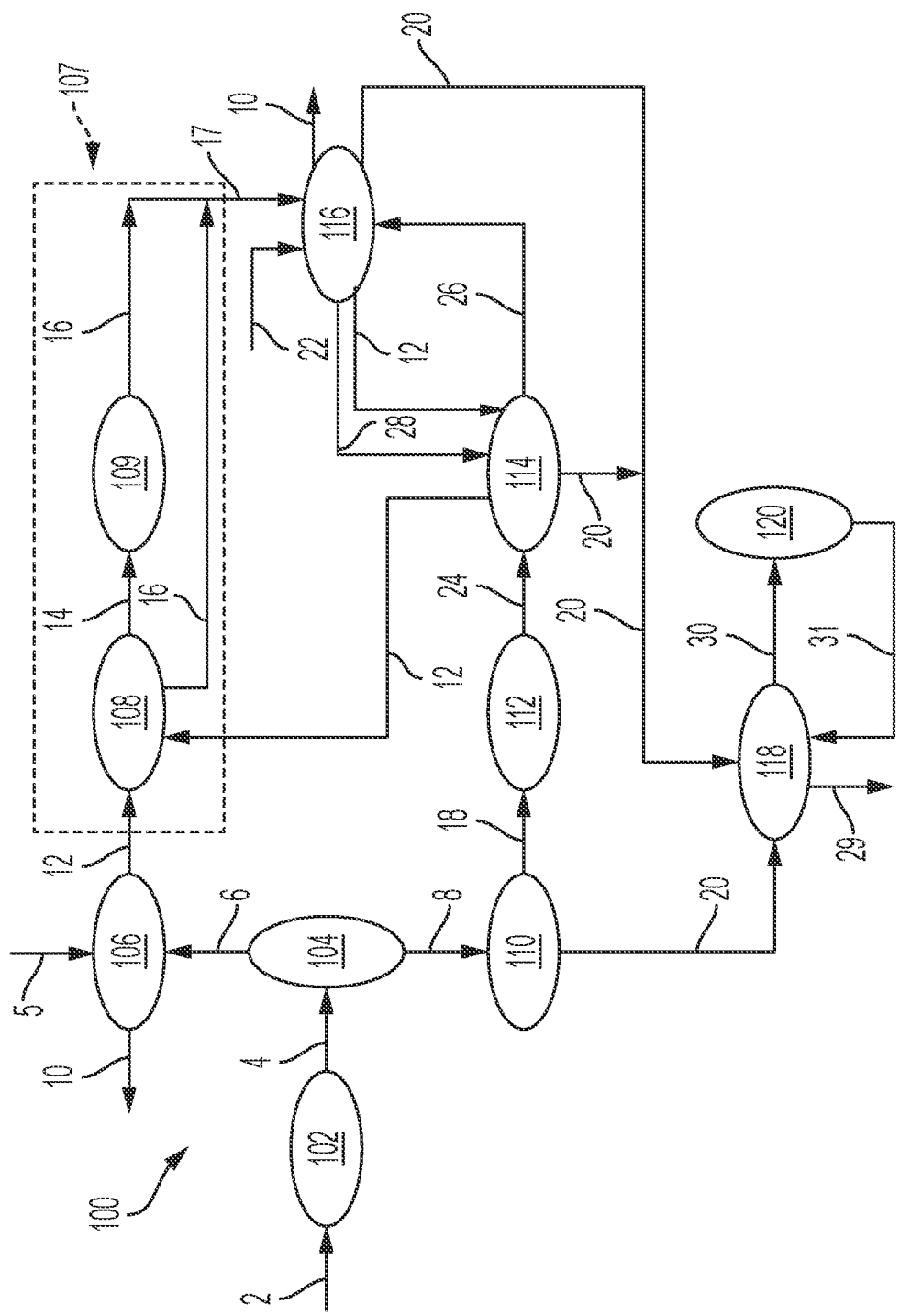
FIG. 1 illustrates a process flow diagram for an exemplary process in accordance with embodiments described herein.

For the purpose of describing the simplified schematic illustrations and descriptions of the relevant figures, the numerous valves, temperature sensors, electronic controllers and the like that may be employed and well known to those of ordinary skill in the art of certain chemical processing operations are not included. Further, accompanying components that are often included in typical chemical processing operations, such as air supplies, catalyst hoppers, and flue gas handling systems, are not depicted. Accompanying components that are in hydrotreating units, such as bleed streams, spent catalyst discharge subsystems, and catalyst replacement sub-systems are also not shown. It should be understood that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines, which may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows, which do not connect two or more system components, signify a product stream, which exits the depicted system, or a system inlet stream, which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that according to the embodiments presented in the relevant figures, an arrow between two system components may signify that the stream is not processed between the two system components. In other embodiments, the stream signified by the arrow may have substantially the same composition throughout its transport between the two system components. Additionally, it should be understood that in embodiments, an arrow may represent that at least 75 wt. %, at least 90 wt. %, at least 95 wt. %, at least 99 wt. %, at least 99.9 wt. %, or even 100 wt. % of the stream is transported between the system components. As such, in embodiments, less than all of the stream signified by an arrow may be transported between the system components, such as if a slip stream is present.

It should be understood that two or more process streams are "mixed" or "combined" when two or more lines intersect in the schematic flow diagrams of the relevant figures. Mixing or combining may also include mixing by directly introducing both streams into a like reactor, separation unit, or other system component. For example, it should be understood that when two streams are depicted as being combined directly prior to entering a separation unit or reactor, that in embodiments the streams could equivalently be introduced into the separation unit or reactor and be mixed in the reactor. Alternatively, when two streams are depicted to independently enter a system component, they may in embodiments be mixed together before entering that system component.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments herein are directed to integrated systems and processes for forming para-xylenes from a naphtha stream, while providing the aforementioned benefits.

As used herein, the term "$C_\#$ hydrocarbons", wherein "#" is a positive integer, is meant to describe all hydrocarbons having #carbon atoms. Moreover, the term "$C_{\#+}$ hydrocarbons" is meant to describe primarily all hydrocarbon molecules having #or more carbon atoms. Accordingly, the term $C_{8+}$ hydrocarbons" is meant to describe a mixture of hydrocarbons containing primarily 8 or more carbon atoms. Similarly, the term "$C_{\#-}$ hydrocarbons" is meant to describe primarily all hydrocarbon molecules having #or less carbon atoms. Similarly, the term "$C_\#$-$C_\#$" hydrocarbons is meant to describe a mixture of hydrocarbon molecules containing primarily between #and #' carbon atoms.

As used herein, a "catalyst" refers to any substance that increases the rate of a specific chemical reaction. Catalysts described in this disclosure may be utilized to promote various reactions, such as, but not limited to, cracking (including aromatic cracking), demetalization, desulfurization, denitrogenation, methylation, disproportionation, dealkylation, dearylation, transalkylation, and isomerization. As used herein, "cracking" generally refers to a chemical reaction where carbon-carbon bonds are broken. For example, a molecule having carbon to carbon bonds is broken into more than one molecule by the breaking of one or more of the carbon to carbon bonds, or is converted from a compound which includes a cyclic moiety, such as a cycloalkane, cycloalkane, naphthalene, an aromatic or the like, to a compound which does not include a cyclic moiety or contains fewer cyclic moieties than prior to cracking.

As used herein, "catalytic reforming" refers to a conversion process in petroleum refining and petrochemical industries. The reforming process generally catalytically converts low octane naphtha distilled from crude oil into higher octane reformate that contains aromatic compounds with a high amount of BTX. Generally, there are four major types of reactions taking place during reforming processes: (1) dehydrogenation of naphthenes to aromatics; (2) dehydrocyclization of paraffins to aromatics; (3) isomerization; and (4) hydrocracking.

As used herein, the term "crude oil" is to be understood to mean a mixture of petroleum liquids, gases, or combinations of liquids and gases, including some impurities such as sulfur-containing compounds, nitrogen-containing compounds and metal compounds that have not undergone significant separation or reaction processes. Crude oils are distinguished from fractions of crude oil. As used herein, the crude oil may be a minimally treated crude oil to provide a hydrocarbon oil feedstock having total metals (Nickel+Vanadium) content of less than 5 parts per million by weight (ppmw) and Conradson carbon residue of less than 5 wt. % Such minimally treated materials may be considered crude oils as described herein.

As used herein, the term "decreased content" of a substance means that a concentration of the substance is greater before passing through a stage of the process under examination than it is after passing through the stage. As used herein, the term "increased content" of a substance means that a concentration of the substance is greater after passing through a stage of the process under examination than before passing through the stage.

It should be understood that an "effluent" generally refers to a stream that exits a system component such as a separation unit, a reactor, or reaction zone, following a particular reaction or separation, and generally has a different composition (at least proportionally) than the stream that entered the separation unit, reactor, or reaction zone.

As used herein, the term "hydrodearylation" refers to a reaction or series of steps to cleave alkyl bridges of non-condensed alkyl-bridged multi-aromatics or heavy alkyl aromatic compounds to form alkyl mono-aromatics, in the presence of a catalyst and hydrogen. "Alkyl bridged non-condensed alkyl aromatic" compounds refer at least two aromatic (or benzene) rings connected by an alkyl bridge group with at least two carbons bridging between the rings, where the aromatic or benzene rings are connected to different carbons of the alkyl bridge group.

As used herein, the term "hydrogen/feed ratio" or "hydrogen-to-feed ratio," or "hydrogen to feed stream ratio" refers to a standard measure of the volume rate of hydrogen circulating through the reactor with respect to the volume of feed. The hydrogen/feed ratio may be determined by comparing the flow volume of a hydrogen stream and the flow volume of a feed stream into a reactor.

As used herein, the term "naphtha" refers to a mixture of substances primarily including $C_5$ to $C_{11}$ hydrocarbons. "Light naphtha," as used herein, is a fraction of naphtha primarily including $C_5$ to $C_6$ hydrocarbons, but which may also include $C_7$ hydrocarbons. As used herein, the term "heavy naphtha" refers to a fraction of naphtha primarily including $C_7$ to $C_{11}$ hydrocarbons.

As used herein, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Exemplary reactors include packed bed reactors such as fixed-bed reactors, and fluidized bed reactors. One or more "reaction zones" may be disposed in a reactor. As used herein, a "reaction zone" refers to an area where a particular reaction takes place in a reactor. For example, a packed bed reactor with multiple catalyst beds may have multiple reaction zones, where each reaction zone is defined by the area of Each catalyst bed.

As used herein, any stream that is referred to as "rich" in some chemical species contains 50% or more by volume or weight of that chemical species, such as from 50% to 100%, or from 50% to 99%, the remaining 1% including trace amounts of other chemical species.

As used herein, a "separation unit" or "separator" refers to any separation device that at least partially separates one or more chemicals that are mixed in a process stream from one another. For example, a separation unit may selectively separate differing chemical species, phases, or sized material from one another, forming one or more chemical fractions. Examples of separation units include, without limitation, distillation columns, flash drums, knock-out drums, knock-out pots, centrifuges, cyclones, filtration devices, traps, scrubbers, expansion devices, membranes, solvent extraction devices, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation. As used herein, one or more chemical constituents may be "separated" from a process stream to form a new process stream. Generally, a process stream may enter a separation unit and be divided, or separated, into two or more process streams of desired composition. Further, in some separation processes, a "lower boiling point fraction" (sometimes referred to as a "light fraction" or "light fraction stream") and a "higher boiling point fraction" (sometimes referred to as a "heavy fraction," "heavy hydrocarbon fraction," or "heavy hydrocarbon fraction stream") may exit the separation unit, where, on average, the contents of the lower boiling point fraction stream have a lower boiling point than the higher boiling point fraction stream. Other streams may fall between the lower boiling point fraction and the higher boiling point fraction, such as a "medium boiling point fraction."

As used throughout this disclosure, "zeolites" may refer to micropore-containing inorganic materials with regular intra-crystalline cavities and channels of molecular dimension. Zeolites generally comprise a crystalline structure, as opposed to an amorphous structure such as what may be observed in some porous materials such as amorphous silica. Zeolites generally include a microporous framework, which may be identified by a framework type. The microporous structure of zeolites (e.g., 0.3 nm to 2 nm pore size) may render large surface areas and desirable size-/shape-selectivity, which may be advantageous for catalysis. The zeolites described may include, for example, aluminosilicates, titanosilicates, or pure silicates. In embodiments, the zeolites described may include micropores (present in the microstructure of a zeolite), and additionally include mesopores. As used throughout this disclosure, micropores refer to pores in a structure that have a diameter of greater than or equal to 0.1 nm and less than or equal to 2 nm, and mesopores refer to pores in a structure that have a diameter of greater than 2 nm and less than or equal to 50 nm. Unless otherwise described herein, the "pore size" of a material refers to the average pore size, but materials may additionally include micropores and/or mesopores having a particular size that is not identical to the average pore size.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. By way of non-limiting example, a referenced "$C_2$-$C_4$ hydrocarbon stream" passing from a first system component to a second system component should be understood to equivalently disclose "$C_2$-$C_4$ hydrocarbons" passing from a first system component to a second system component, and the like.

Referring initially to FIG. 1, an integrated system 100 for the conversion of naphtha feedstocks is illustrated. As used herein, "feedstock" may also be used to refer to "feed stock(s)" or "feed stream(s)." The integrated system 100 may include a catalytic reformer 102, a first separator 104, a solvent extraction unit 106, a toluene upgrading unit 107, a xylene separation unit 110, a dealkylation unit 112, a fourth separator 114, a transalkylation unit 116, a p-xylene separation unit 118, and a xylene isomerization unit 120. The toluene upgrading unit 107 may further include a benzene/toluene separator 108 along with a benzene methylation unit 109, as explained in more detail herein.

The first separator 104 may be fluidly connected to both the catalytic reformer 102 and the solvent extraction unit 106, downstream from the catalytic reformer 102, and upstream from the solvent extraction unit 106. The benzene/toluene separator 108 (which may also be regarded as a second separator 108) may be fluidly connected to the solvent extraction unit 106 and the benzene methylation unit 109, downstream from the solvent extraction unit 106, and upstream from the benzene methylation unit 109. The benzene methylation unit 109 may be fluidly connected to and upstream from the transalkylation unit 116. The xylene separation unit 110 (which may also be regarded as a third separator 110) may be fluidly connected to the first separator 104, the dealkylation unit 112, and the p-xylene separation unit 118. The xylene separation unit 110 may be downstream from the first separator 104, and upstream from the dealkylation unit 112 and the p-xylene separation unit 118. The fourth separator 114 may be fluidly connected to the dealkylation unit 112 and the transalkylation unit 116, downstream from the dealkylation unit 112, and upstream from the transalkylation unit 116.

The p-xylene separation unit 118 (which may also be regarded as a fifth separator) may be fluidly connected to the xylene separation unit 110, the xylene isomerization unit 120, the fourth separator 114, and the transalkylation unit 116. The p-xylene separation unit 118 may also be downstream from the xylene separation unit 110, the fourth separator 114, the transalkylation unit 116, as well as upstream from the xylene isomerization unit 120. The xylene isomerization unit 120 may in turn also be upstream of the p-xylene separation unit 118, i.e., the xylene isomerization unit 120 may recycle its products to the p-xylene separation unit 118.

Still referring to FIG. 1, the catalytic reformer 102 may catalytically reform a naphtha feed stream 2 utilizing a catalytic reformation catalyst to produce a reformate stream 4. The reformate stream 4 may be rich in aromatic compounds, particularly $C_{6+}$ or $C_6$-$C_{12}$ aromatics. As previously described, any stream that is referred to as "rich" in some chemical species contains 50% or more by volume or weight of that chemical species, such as from 50% to 100%, or from 50% to 99%, the remaining 1% including trace amounts of other chemical species.

The catalytic reformer may be operated at an operating temperature in the range of from 450° C. to 600° C. The catalytic reformer 102 may also be operated at an operating pressure in the range of from 0.3 MPa to 7 MPa. The catalytic reformer may also be operated with a liquid hourly space velocity of from 0.1 $hr^{-1}$ to 5 $hr^{-1}$.

The catalytic reformation catalyst may include a support and a precious metal, the support including a silica, alumina, or silica-alumina, and the precious metal including platinum, ruthenium, or both. The reforming catalyst may also be chlorided. The first separator 104 may receive the reformate stream 4 and may separate the same into a $C_1$-$C_7$ hydrocarbon stream and a $C_{8+}$ hydrocarbon stream.

The naphtha feed stream 2 may include a light naphtha or a heavy naphtha. The naphtha feed stream 2 may also include one or more non-hydrocarbon constituents, such as one or more heavy metals, sulfur compounds, nitrogen compounds, inorganic components, or other non-hydrocarbon compounds. The naphtha feed stream 2 may also be a hydrotreated naphtha, hydrotreated light naphtha, or a hydrotreated heavy naphtha, such that at least a portion of the one or more non-hydrocarbon constituents may be removed from the naphtha feed stream 2.

The solvent extraction unit 106 may receive the $C_1$-$C_7$ hydrocarbon stream along with a first solvent 5. The solvent extraction unit 106 may thereby expose the $C_1$-$C_7$ hydrocarbon stream to the first solvent 5, forming a non-aromatic hydrocarbon stream 10 and an aromatics stream 12. The non-aromatic stream may include $C_1$-$C_7$ non-aromatic hydrocarbon gases and hydrogen. The aromatics stream 12 may include toluene and benzene, and may be rich in toluene, benzene, or the combination thereof.

In embodiments, the solvent extraction unit 106 may include one or more extractive distillation columns, one or more absorbent columns, or combinations thereof. The first solvent 5 may include polar solvents, such as but not limited to sulfolane, n-methylpyrrolidone, di-methyl sulfoxide, n-formyl morpholine, polyglycol, or combinations thereof.

The solvent extraction unit 106 may be operated at an operating temperature in the range of from 160° C. to 220° C. The solvent extraction unit 106 may also be operated at an operating pressure in the range of from 0.5 MPa to 20 MPa.

The toluene upgrading unit 107, particularly the benzene/toluene separator 108, may receive the aromatics stream 12 and may thereby separate the aromatics stream 12 into a benzene stream 14 and a toluene stream 16. The benzene methylation unit 109 may receive the benzene stream 14 and may methylate (add a methyl group to) the benzene stream 14 to form additional toluene stream 16. The benzene methylation unit 109 may further combine the additional toluene stream 16 with the other toluene stream 16 from the benzene/toluene separator 108 to form the toluene-rich transalkylation feed stream 17. The toluene upgrading unit 107 may also send the toluene-rich transalkylation feed stream 17 to the transalkylation unit 116, such as through the benzene methylation unit 109. In embodiments, the methylation catalyst may include a support and an active metal. The support may include a protonated ZSM-5 zeolite, a ZSM-5 zeolite, a beta zeolite, or a mordenite zeolite. The active metal may include titanium, rhenium, platinum, molybdenum, magnesium, or combinations thereof. The toluene-rich transalkylation feed stream 17 may also be combined with an external toluene stream where toluene within the system is not at a sufficient level for the desired transalkylation.

The benzene methylation unit 109 unit may be operated at an operating temperature in the range of from 250° C. to 450° C. The benzene methylation unit 109 may also be operated at an operating pressure in the range of from 0.1 MPa to 5 MPa. The benzene methylation unit 109 may also be operated with a liquid hourly space velocity of from 0.1 $hr^{-1}$ to 5 $hr^{-1}$.

Still referring to FIG. 1, the xylene separation unit 110 may receive the $C_{8+}$ hydrocarbon stream 8 and may separate the same into a $C_{9+}$ hydrocarbon stream 18 and a xylene stream 20. The dealkylation unit 112 may receive the $C_{9+}$ hydrocarbon stream 18 and may dealkylate the same utilizing a dealkylation catalyst to form a dealkylated product stream 24. Without being limited by theory, the inclusion of the dealkylation catalyst may operate to remove alkyl groups from heavy aromatic fractions such as $C_9$ aromatic compounds (TMB and/or MEB), $C_{10}$ aromatic compounds (diethyl benzene and/or tetra-methyl benzene), or $C_{11}$ aromatic compounds, thereby forming at least lighter aromatic fractions such as toluene, benzene, and xylenes.

It is also contemplated that the dealkylation catalyst to a lesser extent may remove alkyl groups acting as bridges for bi-aromatics and multi-aromatics, thereby forming mono-aromatics, as shown in the Examples herein. However, this may be viewed as a downside in traditional para-xylene formation, as this reaction may take up some of the capacity for the dealkylation catalyst to convert the MEB and TMB fraction into the lighter aromatic fractions. Accordingly, as described in further detail hereinbelow, a hydro-dearylation catalyst may supplement the dealkylation catalyst to remove some of the burden of the dealkylation catalyst in dealkylating multi-aromatics and concentrate the dealkylation to the more efficient TMB and MEB dealkylation reactions.

The dealkylation unit 112 may be operated at an operating temperature in the range of from 200° C. to 540° C. The dealkylation unit 112 may also be operated at an operating pressure in the range of from 1 MPa to 5 MPa. The dealkylation unit 112 may also be operated with a liquid hourly space velocity of from 0.1 $hr^{-1}$ to 20 $hr^{-1}$. In embodiments including the hydro-dearylation catalyst within the dealkylation unit 112, a hydrogen to feed stream (stream 18) ratio of the dealkylation unit 112 may be from 0.1 to 8.

The dealkylation catalyst may include a mesoporous mordenite zeolite-based catalyst. The dealkylation catalyst may also include a support and an active metal. The support may be selected from the group of a fluorinated zeolite, a mesoporous mordenite zeolite, a mesoporous ZSM-5 zeolite, or both. The active metal may be selected from the group of copper, nickel, molybdenum, tungsten, platinum, palladium, or combinations thereof. The dealkylation catalyst may include from 1 wt. % to 10 wt. % mordenite by weight of the catalyst, such as approximately 4 wt. % mordenite. The dealkylation catalyst may be similar to the disproportionation catalyst, transalkylation catalyst, and isomerization catalyst.

The fourth separator 114 may receive the dealkylated product stream 24, and may separate the same into additional aromatics stream 12, additional xylene stream 20, and a tri-methyl benzene rich stream 26. The additional aromatics stream 12 may be sent to the benzene/toluene separator 108, the additional xylene stream 20 to the p-xylene separation unit 118, and the tri-methyl benzene rich stream 26 to the transalkylation unit 116.

Still referring to FIG. 1, the transalkylation unit 116 may receive the tri-methyl benzene rich stream 26 and the toluene-rich transalkylation feed stream 17. The transalkylation unit 116 may then upgrade the combination of the two streams with a hydrogen stream 22 into a transalkylation product stream, which may include additional xylene stream 20. The transalkylation product stream may also include unconverted tri-methyl benzene and toluene fractions not converted in the initial upgrading. In embodiments, the transalkylation product stream may also include aromatic fractions produced from the disproportionation of toluene and tri-methyl benzene, particularly benzene and tetra-methyl benzene respectively. Without being limited by theory, this may be due to the transalkylation reaction of tri-methyl benzene and toluene being an equilibrium reaction, wherein at least some disproportionation of the involved chemical species occurs when exposed to the transalkylation catalyst. The benzene and unconverted toluene streams may be combined as additional aromatics stream 12. The tetra-methyl benzene and unconverted tri-methyl benzene may be combined as an alkyl benzene stream 28. The alkyl benzene stream 28 and the additional aromatics stream 12 may then be recycled back to the fourth separator 114, wherein further tri-methyl benzene rich stream 26 and aromatics stream 12 may be recycled back to the transalkylation unit 116 and the benzene/toluene separator 108, respectively.

Additionally, without being limited by theory, the efficiency of the transalkylation reactions to produce xylene from TMB and toluene may be impacted by the volumetric ratio of these species entering the transalkylation unit 116, at least because the TMB/toluene transalkylation reaction is an equilibrium reaction, as described above. Accordingly, it is contemplated that a ratio of the toluene-rich transalkylation feed stream to the tri-methylbenzene rich stream may be from 0.3 to 3 in embodiments herein. At ratios less than 0.3, insufficient toluene may be present within the transalkylation unit 116, and thereby less energy efficient TMB disproportionation reactions may dominate the transalkylation unit 116 over transalkylation reactions. At ratios above 3, the reverse may be the case, with the overabundant toluenes undergoing less energy efficient toluene disproportionation reactions. Without being limited be theory, the transalkylation of TMB/toluene may be regarded as more energy efficient due to the products of the reaction being entirely xylene, rather than xylene and a non-xylene aromatic.

The transalkylation catalyst may include a mesoporous mordenite zeolite-based catalyst. The transalkylation catalyst may also include a support and an active metal. The support may be selected from the group of a mesoporous mordenite zeolite, a mesoporous ZSM-5 zeolite, or both. The active metal may be selected from the group of copper, nickel, molybdenum, tungsten, platinum, palladium, or combinations thereof. The transalkylation catalyst may include from 1 wt. % to 10 wt. % mordenite by weight of the catalyst, such as approximately 4 wt. % mordenite. The transalkylation catalyst may be similar to the disproportionation catalyst, dealkylation catalyst, and isomerization catalyst.

The transalkylation unit 116 may be operated at an operating temperature in the range of from 200° C. to 540° C. The transalkylation unit 116 may also be operated at an operating pressure in the range of from 1 MPa to 5 MPa. The transalkylation unit 116 may also be operated with a liquid hourly space velocity of from 0.1 $hr^{-1}$ to 20 $hr^{-1}$. The transalkylation unit 116 may also be operated with a hydrogen to feed stream (streams 17 and 26) ratio of from 0.1 to 8.

Still referring to FIG. 1, the p-xylene separation unit 118 may receive the xylene stream 20 as well as any of the additional xylene stream 20. The p-xylene separation unit 118 may also be operable separate the xylene stream 20 into a para-xylene stream 29 and a xylene isomer stream 30, such as by using adsorption, crystallization, or a combination of both, as may be understood in the art. The xylene isomer stream 30 may include m-xylene and o-xylene isomers. In embodiments, the p-xylene separation unit 118 may include one or more adsorbent columns, one or more crystallization columns, or combinations thereof.

The xylene isomerization unit 120 may receive the xylene isomer stream 30 and may isomerize the same with an isomerization catalyst to form a para-xylene rich stream 31, which may be recycled back to the p-xylene separation unit 118 for further separation of the para-xylene stream 29 and the xylene isomer stream 30.

The xylene isomerization unit 120 may be operated at an operating temperature in the range of from 200° C. to 540° C. The xylene isomerization unit 120 may also be operated at an operating pressure in the range of from 1 MPa to 5 MPa. The xylene isomerization unit 120 may also be operated with a liquid hourly space velocity of from 0.1 $hr^{-1}$ to 20 $hr^{-1}$.

The isomerization catalyst may include a mesoporous zeolite-based catalyst. The isomerization catalyst may also include a support and an active metal. The support may be selected from the group of a mesoporous mordenite zeolite, a mesoporous ZSM-5 zeolite, or beta zeolite. The active metal may be selected from the group of copper, nickel, molybdenum, tungsten, platinum, palladium, or combinations thereof. The isomerization catalyst may include from 1 wt. % to 10 wt. % mordenite by weight of the catalyst, such as approximately 4 wt. % mordenite. The isomerization catalyst may be similar to the disproportionation catalyst, dealkylation catalyst, and transalkylation catalyst, but with different selections for the active metal, as well as the amount of the same.

Figure 2:
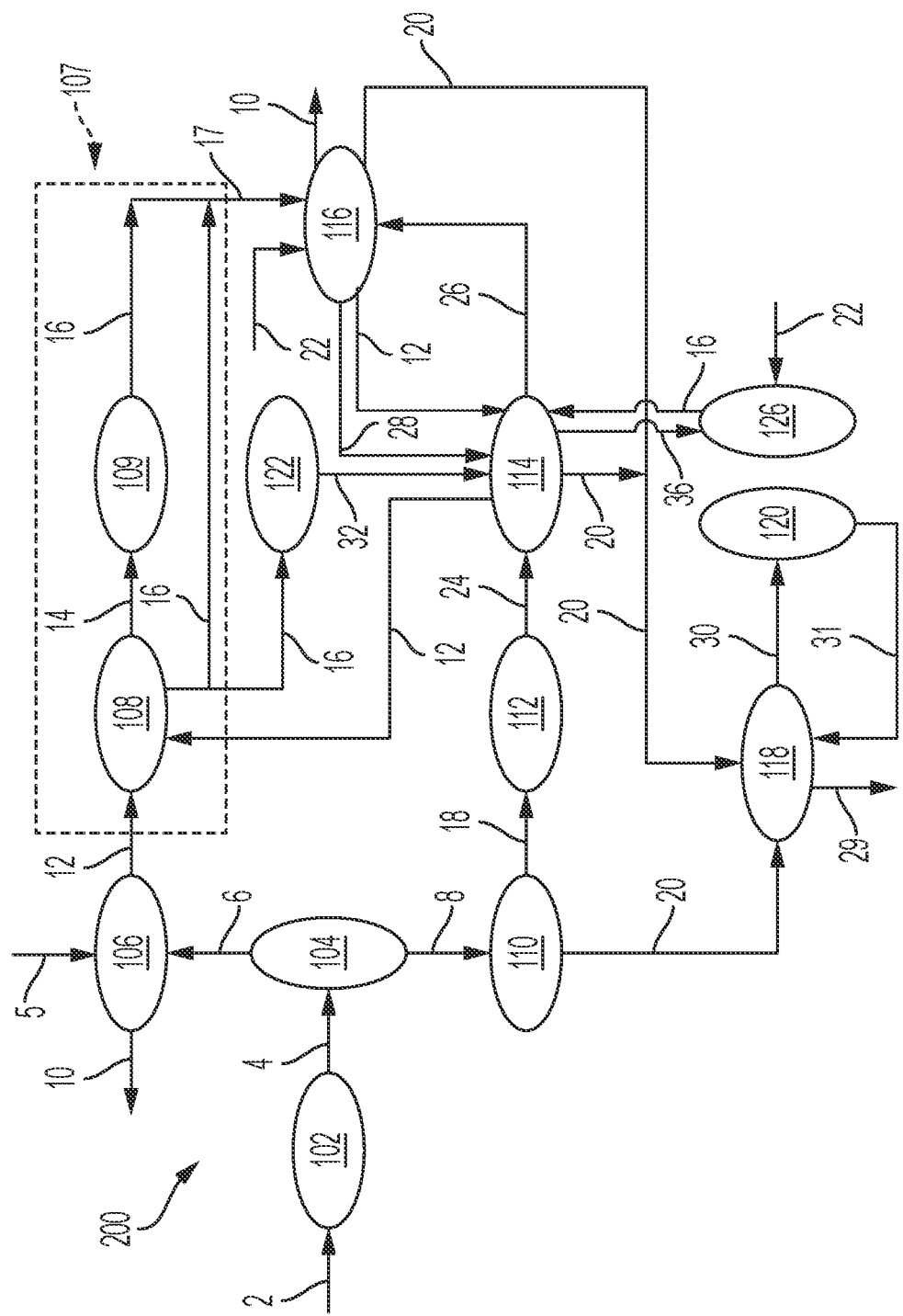
FIG. 2 illustrates another process flow diagram for an exemplary process in accordance with embodiments described herein.

Now referring to FIG. 2, the system 200 may be similar in some or all aspects to the system 100, and may further include one or more additional treatment units or separators, as explained in further detail hereinbelow. For example, and as illustrated in FIG. 2, the system 100 may further include a toluene disproportionation unit 122 including a disproportionation catalyst.

Without being limited by theory, the toluene disproportionation unit 122 may be included in the system 100 to account for an excess of toluene as feed to the transalkylation unit 116. For example, in embodiments, the ratio by weight of the toluene-rich transalkylation feed stream 17 to the tri-methyl benzene rich stream 26 may be from 0.3 to 3.0. However, as this ratio continues to increase, particularly past 1.5, the desired transalkylation rate of TMB and toluene to xylene may decline, with a proportionate increase in disproportionation of toluene to xylene and benzene. Accordingly, the toluene disproportionation unit 122 may be included in the system to alleviate at least a portion of the burden of the transalkylation unit 116 and reduce the ratio within the transalkylation unit 116 to optimized levels.

The disproportionation catalyst may include a mesoporous zeolite-based catalyst. The disproportionation catalyst may also include a support and an active metal. The support may be selected from the group of a mesoporous mordenite zeolite, a mesoporous ZSM-5 zeolite, or both. The active metal may be selected from the group of copper, nickel, molybdenum, tungsten, platinum, palladium, or combinations thereof. The disproportionation catalyst may include from 1 wt. % to 10 wt. % mordenite by weight of the catalyst, such as approximately 4 wt. % mordenite. The disproportionation catalyst may be similar or identical to the transalkylation catalyst, dealkylation catalyst, and isomerization catalyst.

The toluene disproportionation unit 122 may be operated at an operating temperature in the range of from 200° C. to 540° C. The toluene disproportionation unit 122 may also be operated at an operating pressure in the range of from 1 MPa to 5 MPa. The toluene disproportionation unit 122 may also be operated with a liquid hourly space velocity of from 1 $hr^{-1}$ to 20 $hr^{-1}$.

Still referring to FIG. 2, the system 100 may also include a hydro-dearylation unit 126 including a hydro-dearylation catalyst. The hydro-dearylation unit 126 may be fluidly connected to the fourth separator 114, and may be both upstream and downstream of the fourth separator 114. In other words, the hydro-dearylation unit 126 may recycle the products of the unit 126 back to the fourth separator 114. The hydro-dearylation unit 126 may also be configured to receive additional hydrogen stream 22. Without being limited by theory, the inclusion of the hydro-dearylation unit 126 may operate to convert $C_{10+}$ hydrocarbon fractions within the naphtha feed stream 2, particularly those within the $C_{9+}$ hydrocarbon stream 18 and the dealkylated product stream 24, to toluene that may be further upgraded to para-xylene according to the systems and processes herein.

The hydro-dearylation catalyst may include a support selected from one or more of silica, alumina, and titania; an acidic component selected from the group consisting of amorphous silica-alumina and zeolites, the zeolites' framework selected from one or more of FAU, BEA, MOR, MFI, and MWW, and one or more IUPAC Group 6-10 metals selected from the group consisting of iron, cobalt, nickel, molybdenum, and tungsten.

The hydro-dearylation unit 126 may be operated at an operating temperature in the range of from 200° C. to 540° C. The hydro-dearylation unit 126 may also be operated at an operating pressure in the range of from 1 MPa to 5 MPa. The hydro-dearylation unit 126 may also be operated with a liquid hourly space velocity of from 1 $hr^{-1}$ to 20 $hr^{-1}$. The transalkylation unit 116 may also be operated with a hydrogen to feed stream (streams 17 and 26) ratio of from 0.1 to 10.

Figure 3:
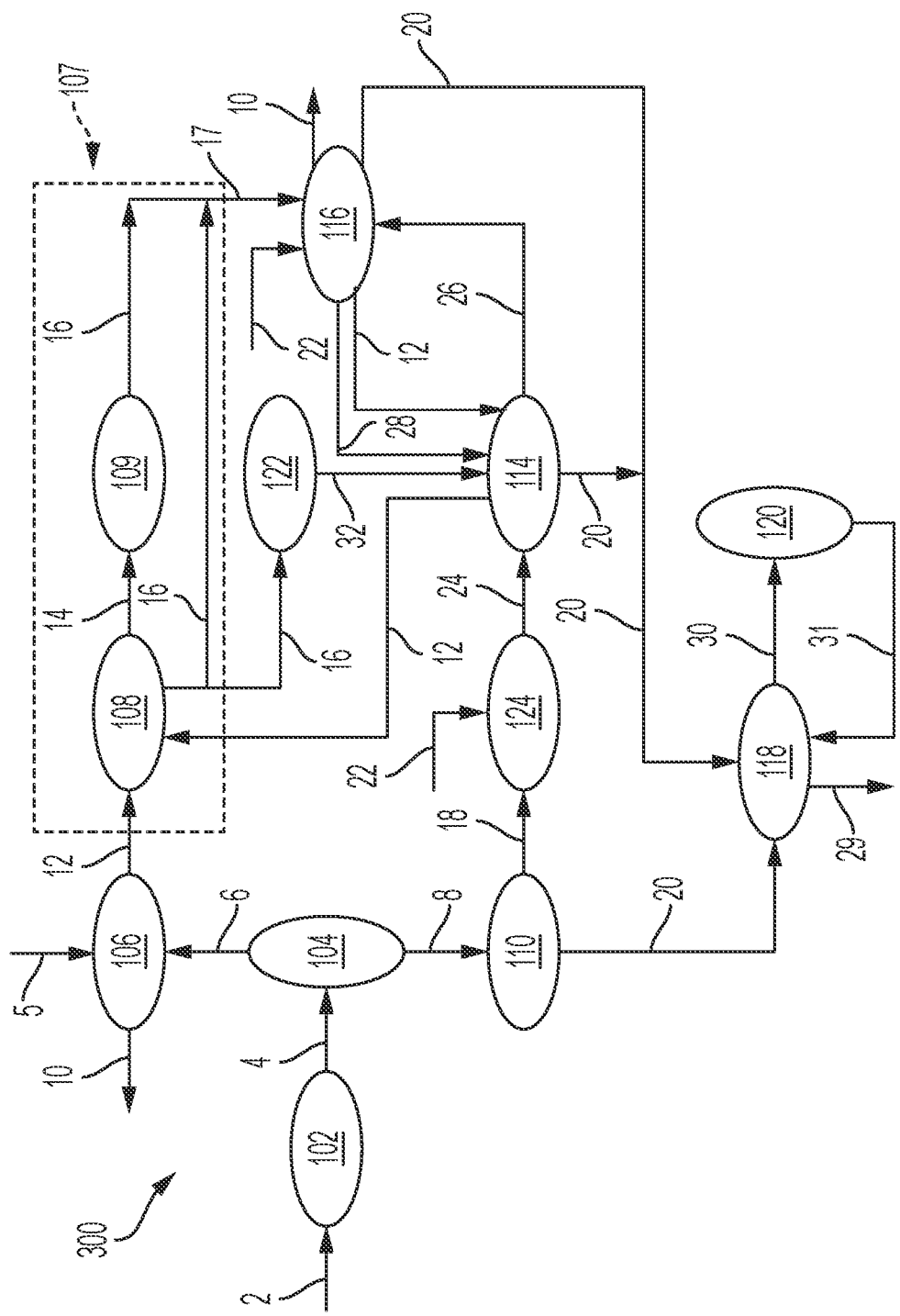
FIG. 3 illustrates another process flow diagram for an exemplary process in accordance with embodiments described herein.

Now referring to FIG. 3, the system 300 may be similar in some or all aspects to the systems 100 and 200, and may further include one or more additional treatment units or separators, as explained in further detail hereinbelow. For example, and as illustrated in FIG. 3, the dealkylation unit 112 may be configured to receive additional hydrogen stream 22, and may further include the hydro-dearylation catalyst, such that the dealkylation unit 112 may be regarded as a hybrid hydro-dearylation/dealkylation unit 124 having a hydro-dearylation function as well as a dealkylation function. Particularly, similar to as mentioned above, the inclusion of the hybrid hydro-dearylation/dealkylation unit 124 may operate to convert $C_{10+}$ hydrocarbon fractions within the naphtha feed stream 2, particularly those within the $C_{9+}$ hydrocarbon stream 18 and the dealkylated product stream 24, to toluene that may be further upgraded to para-xylene according to the systems and processes herein. Moreover, as discussed above, the inclusion of the hydro-dearylation catalyst with the dealkylation catalyst may operate to focus the dealkylation catalyst's activity on dealkylating mono-aromatics, which may in turn improve the yield of xylenes in the dealkylated product stream.

Referring now to FIGS. 1-3, embodiments of the present disclosure also include integrated processes for producing para-xylenes. The processes may include any of the integrated systems 100-300 previously described. The process may include catalytically reforming the naphtha feed stream 2 to form a reformate stream 4, separating the reformate stream 4 into a $C_1$-$C_7$ hydrocarbon stream 6 and a $C_{8+}$ hydrocarbon stream 8, exposing the $C_1$-$C_7$ hydrocarbon stream 6 to the first solvent 5 in the solvent extraction unit 106 to form the non-aromatic hydrocarbon stream 10 and the aromatics stream 12, and upgrading the aromatics stream 12 to form a toluene-rich transalkylation feed stream 17.

The process may further include separating the $C_{8+}$ hydrocarbon stream 8 into the $C_{9+}$ hydrocarbon stream 18 and the xylene stream 20, separating the xylene stream 20 to form the para-xylene stream 29 and the xylene isomer stream 30, and isomerizing the xylene isomer stream 30 with the isomerization catalyst to produce the para-xylene rich stream 31. The process may also include dealkylating the $C_{9+}$ hydrocarbon stream 18 in the dealkylation unit 112 with the dealkylation catalyst, thereby forming the dealkylated product stream 24, separating the dealkylated product stream 24 into additional aromatics stream 12, additional xylene stream 20, and the tri-methyl benzene rich stream 26, and upgrading the toluene-rich transalkylation feed stream 17 and the tri-methyl benzene rich stream 26 in the transalkylation unit 116 with the hydrogen stream 22 and the transalkylation catalyst to produce the alkyl benzene stream 28 and additional amounts of non-aromatic hydrocarbon stream 10, aromatics stream 12, and xylene stream 20. In embodiments, the ratio of the toluene-rich transalkylation feed stream 17 to the tri-methylbenzene rich stream 26 may be from 0.3 to 3.

As previously discussed, the additional streams produced in the various treatment units to enhance the production of para-xylene. For example, and in embodiments, the process may further include combining the additional non-aromatic hydrocarbon stream 10 with the non-aromatic hydrocarbon stream 10; combining the additional aromatics stream 12 with the aromatics stream 12; combining the additional xylene stream 20 and the para-xylene rich stream 31 with the xylene stream 20; and combining the alkyl benzene stream 28 with the dealkylated product stream 24.

As illustrated in FIGS. 2 and 3, upgrading the aromatics stream 12 to form the toluene-rich transalkylation feed stream 17, such as in the toluene upgrading unit 107, may further include separating the aromatics stream 12 into a benzene stream 14 and a toluene stream 16, methylating the benzene stream 14 in the presence of a methylation catalyst to form additional toluene stream 16, and combining the toluene stream 16 and the additional toluene stream 16 to form the toluene-rich transalkylation feed stream 17. The process may also include sending at least a portion of the toluene-rich transalkylation feed stream 17 to the toluene disproportionation unit 122 with the disproportionation catalyst to form a disproportionation unit product stream 32, such as when the ratio of the toluene-rich transalkylation feed stream to the tri-methyl benzene stream is from greater than 1.5 to 3. The disproportionation unit product stream 32 may include additional xylene stream 20 and benzene stream 14.

As illustrated in FIG. 2, the dealkylated product stream 24 may further include a $C_{10+}$ hydrocarbon stream 36. The process may then further include upgrading the $C_{10+}$ hydrocarbon stream 36 with additional hydrogen stream 22 and the hydro-dearylation catalyst to form additional toluene stream 16, and for the benefits previously discussed. Alternatively, as illustrated in FIG. 2, the dealkylation unit 112 may further include the hydro-dearylation catalyst, and the process may further include dealkylating and hydro-dearylating the $C_{9+}$ hydrocarbon stream 18 in the dealkylation unit 112 in the presence of additional hydrogen stream 22, thereby forming additional xylene stream 20 and additional aromatics stream 12.

EXAMPLES

The various embodiments of processes and systems for the conversion of a naphtha feed stream into para-xylenes will be further clarified by the following examples. The examples are illustrative in nature, and should not be understood to limit the subject matter of the present disclosure.

Two simulations in Aspen Plus software were conducted according to the according to the embodiments previously discussed and illustrated in FIGS. 2 and 3. The results of the simulation using the configuration in FIG. 2 are shown below in Table 1. Although not illustrated in Table 1, a hydrogen stream was also introduced to the hydro-dearylation reactor at a ratio of approximately 40 parts per thousand hydrogen to $C_{10+}$ feed. As shown in Table 1, the configuration illustrated in FIG. 2 resulted in a large percentage of the initial feed being converted to p-xylene fractions, with only a minor amount of $C_{10+}$ fractions remaining untreated.

TABLE 1

| Mass Flows of Configuration 1 (FIG. 2) | | | | | | | | | | | | | |
|---|---|---|---|---|---|---|---|---|---|---|---|---|---|
| | | Catalytic Reformation | | Solvent Extraction | | B/T Separator | | Benzene Methylation | | Dispropor- tionation | | Trans- alkylation | |
| Mass Flows Total | Units kg/hr | Feed 1698 | Product 1698 | Feed 363 | Product 363 | Feed 1360 | Product 1345 | Feed 134 | Product 158 | Feed 12 | Product 12 | Feed 2469 | Product 2712 |
| H2 | kg/hr | 0 | | | | | | | | | | 100 | 198 |
| Light Gas | kg/hr | 101 | 101 | 101 | 101 | | | | | | | | 200 |
| Benzene | kg/hr | 49 | 49 | 49 | 49 | 149 | 134 | 134 | 158 | | 5 | | 71 |
| Toluene | kg/hr | 213 | 213 | 213 | 213 | 1211 | 1211 | | | 12 | | 1357 | 765 |
| P-Xylene | kg/hr | 97 | 97 | | | | | | | | 2 | | 170 |
| C8 (no P-Xyl) | kg/hr | 291 | 291 | | | | | | | | 5 | | 728 |
| MEB | kg/hr | 211 | 211 | | | | | | | | | 5 | 3 |
| TMB | kg/hr | 565 | 565 | | | | | | | | | 1007 | 503 |
| C10+ | kg/hr | 171 | 171 | | | | | | | | | | 74 |
| | | Xylene Separator | | Dealkylation | | Fourth Separator | | Hydro- Dearylation | | P-xylene separation | | Isomerization | |
| Mass Flows Total | Units kg/hr | Feed 6557 | Product 6169 | Feed 947 | Product 959 | Feed 3493 | Product 3271 | Feed 73 | Product 73 | Feed 6237 | Product 6237 | Feed 4834 | Product 4834 |
| H2 | kg/hr | | | | 7 | 103 | | | | | | | |
| Light Gas | kg/hr | | | | 79 | 140 | | | | | | | |
| Benzene | kg/hr | | | | 24 | 73 | 100 | | | | | | |
| Toluene | kg/hr | | | | 160 | 1003 | 998 | | 73 | | | | |
| P-Xylene | kg/hr | 1306 | 1209 | | 22 | 192 | 194 | | | 1403 | 1403 | | 1112 |
| C8 (no P-Xyl) | kg/hr | 4304 | 4013 | | 88 | 818 | 821 | | | 4834 | 4834 | 4834 | 3722 |

TABLE 1-continued

| Mass Flows of Configuration 1 (FIG. 2) | | | | | | | | |
|---|---|---|---|---|---|---|---|---|
| MEB | kg/hr | 211 | 211 | 211 | 3 | 11 | 5 | |
| TMB | kg/hr | 565 | 565 | 565 | 503 | 1006 | 1007 | |
| C10+ | kg/hr | 171 | 171 | 171 | 73 | 147 | 146 | 73 |

The results of the simulation using the configuration in FIG. 3 is shown below in Table 2. As shown in Table 2, feed for the system included a relatively greater proportion of $C_{10+}$ hydrocarbon fractions to test the capability of the hybrid hydro-dearylation/dealkylation unit with both hydro-dearylation and dealkylation catalysts. As shown in Table 2, the configuration illustrated in FIG. 3 also resulted in a large percentage of the initial feed being converted to p-xylene fractions, with only a minor amount of $C_{10+}$ fractions remaining untreated. The configuration illustrated in FIG. 3 also achieved the conversion of relatively greater amount of the $C_{10+}$ hydrocarbon fractions without the need for a separate hydro-dearylation unit, instead using the hybrid hydro-dearylation/dealkylation unit. An identical hydrogen stream was added for the hybrid reactor as for the hydro-dearylation unit in Table 1.

TABLE 2

| Mass Flows of Configuration 2 (FIG. 3) | | | | | | | | | | | | | |
|---|---|---|---|---|---|---|---|---|---|---|---|---|---|
| | | Catalytic Reformation | | Solvent Extraction | | B/T Separator | | Benzene Methylation | | Dispropor- tionation | | Trans- alkylation | |
| Mass Flows | Units | Feed | Product | Feed | Product | Feed | Product | Feed | Product | Feed | Product | Feed | Product |
| Total | kg/hr | 1898 | 1898 | 363 | 363 | 1649 | 1633 | 143 | 169 | 15 | 15 | 2756 | 3008 |
| H2 | kg/hr | 0 | | | | | | | | | | 100 | 198 |
| Light Gas | kg/hr | 101 | 101 | 101 | 101 | | | | | | | | 220 |
| Benzene | kg/hr | 49 | 49 | 49 | 49 | 159 | 143 | 143 | 169 | | 6 | | 80 |
| Toluene | kg/hr | 213 | 213 | 213 | 213 | 1490 | 1490 | | | 15 | | 1644 | 917 |
| P-Xylene | kg/hr | 97 | 97 | | | | | | | | 3 | | 191 |
| C8 (no P-Xyl) | kg/hr | 291 | 291 | | | | | | | | 6 | | 814 |
| MEB | kg/hr | 211 | 211 | | | | | | | | | 5 | 3 |
| TMB | kg/hr | 565 | 565 | | | | | | | | | 1007 | 503 |
| C10+ | kg/hr | 371 | 371 | | | | | | | | | | 82 |

| | | Xylene Separator | | Hybrid Hydro- Dearylation Dealkylation Unit | | Fourth Separator | | P-xylene separation | | Isomerization | |
|---|---|---|---|---|---|---|---|---|---|---|---|
| Mass Flows | Units | Feed | Product | Feed | Product | Feed | Product | Feed | Product | Feed | Product |
| Total | kg/hr | 6749 | 6749 | 1147 | 1159 | 3929 | 3929 | 6725 | 6725 | 5214 | 5214 |
| H2 | kg/hr | | | | 7 | 103 | 103 | | | | |
| Light Gas | kg/hr | | | | 79 | 150 | 150 | | | | |
| Benzene | kg/hr | | | | 24 | 110 | 110 | | | | |
| Toluene | kg/hr | | | | 360 | 1277 | 1277 | | | | |
| P-Xylene | kg/hr | 1296 | 1296 | | 22 | 216 | 216 | 1511 | 1511 | | 1199 |
| C8 (no P-Xyl) | kg/hr | 4306 | 4306 | | 88 | 908 | 908 | 5214 | 5214 | 5214 | 4015 |
| MEB | kg/hr | 211 | 211 | 211 | 3 | 6 | 6 | | | | |
| TMB | kg/hr | 565 | 565 | 565 | 503 | 1006 | 1006 | | | | |
| C10+ | kg/hr | 371 | 371 | 371 | 73 | 155 | 155 | | | | |

Testing was also conducted of the mesoporous mordenite catalyst that may be used in the dealkylation reactor, as shown below in Table 3. The catalyst had a mordenite content of approximately 4 wt. % by weight of the catalyst. The feed was approximately 60 wt. % $C_{9+}$ hydrocarbon fractions and 40 wt. % toluene. As shown in Table 3, the mesoporous mordenite catalyst illustrated a greater conversion rate to xylene than a comparable ZSM-5 zeolite catalyst, as well as a greater conversion rate of methyl-ethyl-benzenes present in the $C_{9+}$ hydrocarbon fraction.

TABLE 3

| Dealkylation Testing of Mesoporous Mordenite Catalyst | | | | | | | |
|---|---|---|---|---|---|---|---|
| Temperature ° C. | Zeolite | Xylenes wt % | C1-C4 Hydrocarbons wt % | Conv_MEB [%] | Conv_TMB [%] | Conv_Toluene [%] | Conv_AC9 [%] |
| 400 | Mesoporous Mordenite | 37 | 8.9 | 93.17 | 53.9 | 27.61 | 64.43 |

TABLE 3-continued

Dealkylation Testing of Mesoporous Mordenite Catalyst

| Temperature °C. | Zeolite | Xylenes wt % | C1-C4 Hydrocarbons wt % | Conv_MEB [%] | Conv_TMB [%] | Conv_Toluene [%] | Conv_AC9 [%] |
|---|---|---|---|---|---|---|---|
| 450 | Mesoporous Mordenite | 32 | 16.1 | 95.8 | 62.42 | 32.55 | 71.4 |
| 360 | Mesoporous ZSM-5 | 19 | 5.74 | 91.88 | 25.27 | 0.58 | 43.15 |
| 400 | Mesoporous ZSM-5 | 28 | 7.76 | 98.26 | 45.7 | 4.89 | 59.8 |

Similarly, testing was also conducted of the mesoporous mordenite catalyst within the transalkylation unit. The catalyst had a mordenite content of approximately 4 wt. % by weight of the catalyst. Feed for the transalkylation unit is shown below in Table 4, with the results shown in Table 5. As shown in Table 5, the mesoporous mordenite catalyst showed the ability to reliably convert MEB and TMB's into xylenes.

TABLE 4

Feed Composition for Transalkylation Testing

| Feed | (wt. %) |
|---|---|
| Benzene | 0.00 |
| Toluene | 0.05 |
| PX | 0.38 |
| C8 (no px) | 5.31 |
| MEB | 21.32 |
| TMB | 56.10 |
| C10+ and other components | 16.83 |

TABLE 5

Transalkylation Testing of Mesoporous Mordenite Catalyst

| Pressure MPa | Benzene wt. % | Toluene wt. % | Xylenes wt. % | TMB wt. % | MEB wt. % | C10 Hydrocarbons wt. % | C11+ Hydrocarbons wt. % |
|---|---|---|---|---|---|---|---|
| 1 | 1.77 | 13.06 | 30.54 | 40.19 | 1.13 | 11.36 | 0.41 |
| 2 | 1.52 | 13.82 | 36.61 | 35.27 | 0.63 | 9.95 | 0.17 |
| 3 | 1.58 | 14.33 | 37.33 | 34.57 | 0.49 | 9.07 | 0.12 |

Finally, testing was also conducted of the mesoporous mordenite catalyst within the toluene disproportionation unit, with the results shown in Table 6. The catalyst had a mordenite content of approximately 4 wt. % by weight of the catalyst. As shown in Table 6, the mesoporous mordenite catalyst also showed the ability to reliably convert toluene into xylene and benzene.

TABLE 6

Dealkylation Testing of Mesoporous Mordenite Catalyst

| Time on Stream hours | Temperature °C. | Unconverted Toluene wt. % | Xylene wt. % | C1-C5 Hydrocarbons wt. % | Benzene wt. % | Ethyl Benzene wt. % | C9+ Hydrocarbons wt. % |
|---|---|---|---|---|---|---|---|
| 2 | 400 | 52.67 | 21.3 | 1 | 20.87 | 0.42 | 2.97 |
| 4 | 400 | 45.23 | 24.62 | 1.1 | 24 | 0.55 | 3.88 |
| 20 | 400 | 44.22 | 25.16 | 1.35 | 24.03 | 0.43 | 4.22 |
| 25 | 400 | 44.35 | 25.15 | 0.83 | 24.41 | 0.55 | 4.08 |
| 28 | 400 | 44.69 | 25.1 | 0.77 | 23.85 | 0.55 | 4.01 |
| 40 | 400 | 44.88 | 25.27 | 0.63 | 23.86 | 0.56 | 4.15 |
| 42 | 400 | 44.18 | 24.89 | 0.76 | 24.81 | 0.57 | 4.07 |
| 60 | 400 | 44.42 | 24.8 | 0.78 | 24.8 | 0.57 | 4.07 |

It is noted that recitations in the present disclosure of a component of the present disclosure being "operable" or "sufficient" in a particular way, to embody a particular property, or to function in a particular manner, are structural recitations, as opposed to recitations of intended use. More specifically, the references in the present disclosure to the manner in which a component is "operable" or "sufficient" denotes an existing physical condition of the component and, as such, is to be taken as a definite recitation of the structural characteristics of the component.

It is also noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Having described the subject matter of the present disclosure in detail and by reference to specific embodiments, it is noted that the various details disclosed in the present disclosure should not be taken to imply that these details relate to elements that are essential components of the various embodiments described in the present disclosure. Further, it will be apparent that modifications and variations are possible without departing from the scope of the present disclosure, including, but not limited to, embodiments defined in the appended claims.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more instances or components. It is to be understood that the words "first" and "second" serve no other purpose and are not part of the name or description of the component, nor do they necessarily define a relative location, position, or order of the component. Furthermore, it is to be understood that the mere use of the term "first" and "second" does not require that there be any "third" component, although that possibility is contemplated under the scope of the present disclosure.

What is claimed is:

1. An integrated process for producing para-xylenes, the process comprising:
   catalytically reforming a naphtha feed stream to form a reformate stream;
   separating the reformate stream into a $C_1$-$C_7$ hydrocarbon stream and a $C_{8+}$ hydrocarbon stream;
   exposing the $C_1$-$C_7$ hydrocarbon stream to a first solvent in a solvent extraction unit to form a non-aromatic hydrocarbon stream and an aromatics stream;
   separating the aromatics stream into a benzene stream and a toluene stream;
   methylating the benzene stream in the presence of a methylation catalyst to form additional toluene stream;
   combining the toluene stream and the additional toluene stream to form a toluene-rich transalkylation feed stream;
   separating the $C_{8+}$ hydrocarbon stream into a $C_{9+}$ hydrocarbon stream and a xylene stream comprising ortho-xylene, meta-xylene, and para-xylene;
   separating the xylene stream into a para-xylene stream and a xylene isomer stream comprising ortho-xylene and meta-xylene;
   isomerizing the xylene isomer stream with a isomerization catalyst to produce a para-xylene rich stream;
   dealkylating the $C_{9+}$ hydrocarbon stream in an dealkylation unit with a dealkylation catalyst, thereby forming a dealkylated product stream;
   separating the dealkylation product stream into an additional aromatics stream, an additional xylene stream, and a tri-methyl benzene rich stream; and
   upgrading the toluene-rich transalkylation feed stream and the tri-methyl benzene rich stream in a transalkylation unit with a hydrogen stream and a transalkylation catalyst to produce an alkyl-benzene stream and additional amounts of non-aromatic hydrocarbon stream, aromatics stream, and xylene stream, and wherein:
   a ratio by weight of the toluene-rich transalkylation feed stream to the tri-methylbenzene rich stream is from 0.3 to 3.

2. The process of claim 1, further comprising:
   combining the additional non-aromatic hydrocarbon stream with the non-aromatic hydrocarbon stream;
   combining the additional aromatics stream with the aromatics stream;
   combining the additional xylene stream and the para-xylene rich stream with the xylene stream; and
   combining the alkyl-benzene stream with the dealkylation product stream.

3. The process of claim 2, wherein:
   the dealkylation catalyst comprises:
     a support selected from the group consisting of a fluorinated zeolite, a mesoporous ZSM-5 zeolite, and a mesoporous mordenite zeolite, and
     an active metal selected from the group consisting of cobalt, nickel, and palladium;
   the dealkylation unit further comprises a hydro-dearylation catalyst, comprising:
     a support selected from one or more of silica, alumina, and titania,
     an acidic component selected from the group consisting of amorphous silica-alumina and zeolites, the zeolites' framework selected from one or more of FAU, BEA, MOR, MFI, and MWW, and
     one or more IUPAC Group 6-10 metals selected from the group consisting of iron, cobalt, nickel, molybdenum, and tungsten; and
   the process further comprises dealkylating and hydro-dearylating the $C_{9+}$ hydrocarbon stream in the dealkylation unit in the presence of additional hydrogen stream, thereby forming additional xylene stream and aromatics stream.

4. The integrated process of claim 3, wherein:
   the ratio of the toluene-rich transalkylation feed stream to the tri-methyl benzene stream is from greater than 1.5 to 3; and
   the process further comprises sending at least a portion of the toluene-rich transalkylation feed stream to a disproportionation unit with a disproportionation catalyst to form additional xylene stream and benzene stream.

5. The process of claim 4, wherein:
   the dealkylation, transalkylation, isomerization, and disproportionation occur at a temperature of from 200° C. to 540° C., pressure of from 1 MPa to 5 MPa, and a liquid hourly space velocity of from 0.1 hr$^{-1}$ to 20 hr$^{-1}$; and
   the transalkylation and the dealkylation occur with a hydrogen to feed ratio of from 0.1 to 8.

6. The process of claim 2, wherein:
   the dealkylation product stream further comprises a $C_{10+}$ hydrocarbon stream;
   the process further comprises upgrading the $C_{10+}$ hydrocarbon stream with additional hydrogen stream and a hydro-dearylation catalyst to form additional toluene stream; and
   the hydro-dearylation catalyst comprises:
     a support selected from one or more of silica, alumina, and titania,
     an acidic component selected from the group consisting of amorphous silica-alumina and zeolites, the zeolites' framework selected from one or more of FAU, BEA, MOR, MFI, and MWW, and
     one or more IUPAC Group 6-10 metals selected from the group consisting of iron, cobalt, nickel, molybdenum, and tungsten.

7. The integrated process of claim 6, wherein:
   the ratio by weight of the toluene-rich transalkylation feed stream to the tri-methyl benzene stream is from greater than 1.5 to 3; and
   the process further comprises sending at least a portion of the toluene-rich transalkylation feed stream to a disproportionation unit with a disproportionation catalyst to form additional xylene stream and benzene stream.

8. The process of claim 7, wherein:
   the dealkylation, transalkylation, isomerization, disproportionation, and hydro-dearylation occur at a temperature of from 200° C. to 540° C., pressure of from 1 MPa to 5 MPa, and a liquid hourly space velocity of from 0.1 $hr^{-1}$ to 20 $hr^{-1}$; and the transalkylation and the hydro-dearylation occur with a hydrogen to feed ratio of from 0.1 to 8.

9. The process of claim 2, wherein:

the ratio of the toluene-rich transalkylation feed stream to the tri-methyl benzene stream is from greater than 1.5 to 3; and the process further comprises sending at least a portion of the toluene stream, the additional toluene stream, or the toluene-rich transalkylation feed stream to a disproportionation unit with a disproportionation catalyst to form additional xylene stream and benzene stream.

10. The process of claim 9, wherein the disproportionation catalyst comprises:

a support selected from the group consisting of a mesoporous ZSM-5 zeolite and a mesoporous mordenite zeolite; and an active metal selected from the group consisting of copper, nickel, molybdenum, tungsten, platinum, palladium, or combinations thereof.

11. The process of claim 1, wherein the methylation catalyst comprises a protonated ZSM-5 zeolite.

12. The process of claim 1, wherein:

the reforming catalyst comprises a support and a precious metal, the support comprising silica, alumina, or silica-alumina, and the precious metal comprising platinum, ruthenium, or both;

the first solvent comprises sulfolane, n-methylpyrrolidone, di-methyl sulfoxide, n-formyl morpholine, polyglycol, or combinations thereof;

the dealkylation catalyst, the transalkylation catalyst, and the isomerization catalyst comprise:

a support selected from the group consisting of a fluorinated zeolite, a mesoporous ZSM-5 zeolite, and a mesoporous mordenite zeolite, and an active metal selected from the group consisting of copper, nickel, molybdenum, tungsten, platinum, palladium, or combinations thereof.

13. The process of claim 1, wherein the naphtha feed stream is a hydrotreated naphtha stream.

* * * * *